United States Patent [19]

Martini et al.

[11] 3,997,609
[45] Dec. 14, 1976

[54] PARTIALLY FLUORINATED AMINO ETHERS

[75] Inventors: Thomas Martini, Neuenhain, Taunus; Siegfried Benninger, Schwalbach, Taunus, both of Germany

[73] Assignee: Hoechst Aktiengesellschaft, Frankfurt am Main, Germany

[22] Filed: Feb. 7, 1974

[21] Appl. No.: 440,569

[30] Foreign Application Priority Data

Feb. 9, 1973 Germany .......................... 2306464

[52] U.S. Cl. ............................. 260/584 C; 204/81; 257/78.1
[51] Int. Cl.² ........................................ C07C 93/02
[58] Field of Search ................................ 260/584 C

[56] References Cited

UNITED STATES PATENTS

| | | | |
|---|---|---|---|
| 2,713,593 | 7/1955 | Brice et al. ................ | 260/584 C X |
| 3,766,274 | 10/1973 | Anello et al. ................. | 260/584 C |
| 3,882,178 | 5/1975 | Benninger et al. ........ | 260/584 C X |

Primary Examiner—Paul F. Shaver
Attorney, Agent, or Firm—Curtis, Morris & Safford

[57] ABSTRACT

By reacting tertiary amines carrying hydroxyethyl or 2-hydroxypropyl groups with hexafluoropropene in an aprotic solvent in the presence of a basic catalyst such as triethylamine the hexafluoropropyl ether of the starting compound containing the group

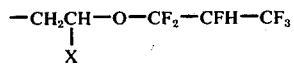

with X = CH$_3$ or H is obtained.

7 Claims, No Drawings

PARTIALLY FLUORINATED AMINO ETHERS

The subject of the present invention is fluorine-containing tertiary amines having the formula

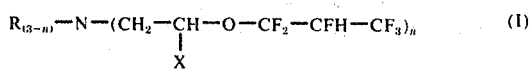  (I)

wherein $n$ represents an integer from 1 to 3, X is hydrogen or $CH_3$ and R represents identical or different, preferably identical straight-chain, branched or cyclic alkyl groups - preferably straight-chain alkyl groups having from 1 to 12, preferably from 1 to 8, particularly from 1 to 4 carbon atoms, or if $n$ is 2, R represents the group $—R'—N—(CH_2CH_2OCF_2CFHCF_3)_2$, $—R'—$ representing an alkylene group having a number of carbon atoms within the range specified for R, especially the ethylene group or the hexa-methylene-group.

The subject matter of the present invention particularly comprises the following compounds falling within the scope of formula I:

tris-[β-(2H-hexafluoropropoxy-ethyl)]-amine, di-[β-(2H-hexafluoropropoxy-ethyl)]-methylamine, -ethylamine, -n-propylamine, -isopropylamine, -n-butylamine, -isobutylamine, -n-hexylamine, -cyclohexylamine, -isononylamine, -n-dodecyl-amine, mono-[β-(2H-hexafluoropropoxy-ethyl)]-dimethylamine, -diethylamine, -methylethylamine, -di-n-propylamine, -di-n-butylamine, -methyl-n-butylamine, -ethyl-n-hexylamine, -dinonylamine, -methyl-dodecyl-amine, -methylcyclohexylamine, tetra-[β-(2H-hexafluoropropoxyethyl)]-ethylene-diamine, -tetra-methylene-diamine, -hexamethylene-diamine, as well as the corresponding mono-, di- and tri-[β(2H-hexafluoro-propoxy-isopropyl]-amines, or tetra-[β-(2H-hexafluoropropoxy-isopropyl)]ethylene-diamine, -tetramethylene diamine, -hexamethylene-diamine.

The compounds are liquids insoluble in water and are of easily mobile to highly viscous consistency. They represent valuable initial products for preparing the corresponding perfluorinated compounds, for example, by electrofluorination. They make good solvents or solubilizers, especially for fluorine-containing organic compounds. In particular they are, however, excellent catalysts for oligomerization, especially for dimerization and trimerization of hexafluoropropene according to copending Application Ser. No. 440,568 (German Application No. P 2306439.3) filed concurrently herewith.

Therefore, the invention concerns also the use of the compounds having formula I as catalysts for oligomerizing hexafluoropropene.

The subject matter of the invention further comprises a process for preparing compounds having formula I, which comprises reacting compounds having the formula

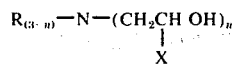  (II)

in the presence of basic catalysts, preferably in an aprotic solvent, with hexafluoropropene. The reaction temperatures range from −30° to +100° C, preference is given to reaction temperatures of from −10° to +60° C, especially from 0° to +50° C.

R, X and $n$ in formula II have the same meaning as in formula I. As basic catalysts there may be used especially organic nitrogen bases, particularly tertiary alkylamines with alkyl groups having from 1 – 6, preferably from 2 to 4 carbon atoms. The alkyl groups of dialkyl amines and trialkyl-amines may be identical or different and two of these alkyl groups can form a ring with 4 to 5 carbon atoms.

Most preferred basic catalysts are trimethyl-amine, triethyl-amine, tri-n-propylamine, tri-n-butylamine, N,N,N',N'-tetramethylethylene-diamine, -hexamethylene-diamine, diazobicyclo[2,2,2]octane. Generally, the quantity of amine to be used is at least 0.1 mole, preferably 0.25 to 0.5 mole for each OH-equivalent to be reacted. Though it is possible to use larger quantities, for example up to 1 mole per each OH-equivalent, there is no advantage in it.

Suitable aprotic solvents are polar solvents; for example nitriles such as acetonitrile, propionitrile and higher nitriles, ethers such as diisopropyl ether, glycol-dimethyl ether, tetrahydrofurane, dioxane, esters such as ethyl acetate, dimethyl phthalate, furthermore dimethyl sulfoxide, dimethyl formamide, dimethyl acetamide, diethyl acetamide, phosphoric acid-tris-(dimethylamide) and -tris-(diethylamide).

It is most useful to employ the solvent in quantities of from 0.2 to 10 parts by volume — calculated on the ethanolamine having formula II.

The reaction pressure is not critical, preference is, however, given to a pressure at or slightly above atmospheric pressure. The process offers the special advantage that it can be carried out at normal pressure. The reaction time depending on the temperature and apparatus used, may be between 3 and 6 hours.

Under these reaction conditions the hexafluoropropene is readily added on the ethanolamines, so that generally approximately stoichiometric quantities are satisfactory, a certain excess of hexafluoropropene of up to 20 %, preferably from 5 to 10 %, being possible. A suitable mode of reaction (for example a cascade arrangement) permits completion of the reaction of any hexafluoropropene that remains unreacted in the first run, by introducing the same into a fresh reaction mixture.

A simple method for preparing the compounds according to the invention may consist, for example, in introducing first into the reaction vessel the corresponding amino-alcohol having formula II in one of the specified solvents, together with the alkylamine, and in subsequently introducing hexafluoro-propene at reaction temperature until an IR-spectroscopic control does not detect any more than free OH—groups. This process includes retaining unreacted hexafluoropropene in known manner by a suitable cooling device and feeding it back into the reaction mixture. It is useful to control the quantity of hexafluoropropene added so as to guarantee that the reflux from the cooling device does not lower the reaction temperature below the desirable level. The reaction products may be submitted to distillation for purification. However, since such a processing step sometimes involves a partial thermal decomposition and the net yield is thus reduced, an aqueous work-up is usually considered to be sufficient; the products are water-washed several times so as to free them from adhering catalyst. Subsequently the product is dried with e.g., $Na_2SO_4$ and optionally maintained at high vacuum for a while.

For the preparation of ultra-pure 2H-hexafluoropropyl ethers absolutely devoid of bases a column chromatographic purification is recommended, carried out advantageously with neutral silica gel as the stationary phase and acetic acid ethyl ester / petroleum ether (boiling point: 75° – 100° C), proportion by volume 1 : 1, as the mobile phase.

The reactions provide good yields, the structure of the products obtained was demonstrated by analytical data, determination of molecular weights and by IR- and H-NMR-spectroscopy.

The products are obtained practically pure. Minor impurities of olefinic fractions which may be found sometimes, have no influence whatsoever on the products being used as catalysts or on their electrofluorination.

The following examples illustrate the invention:

EXAMPLES

EXAMPLE 1

In an agitator flask with thermometer, gas inlet and condenser maintained at about 20° C by a cooling device, 75 g of triethanolamine are dissolved in 500 ml of acetonitrile and mixed with 100 ml of triethylamine. Hexafluoropropene is introduced at 0° C at the same rate as that at which it is used up and until the IR-spectrum ceases to show any OH-bands. The reaction mixture is poured into 500 ml of ice water, the organic phase separated, washed twice with 500 ml of $H_2O$ and finally dried with $Na_2SO_4$.

Yield: 260 g (86.3 % of theory)

The obtained product may be submitted to chromatography for further purification on neutral silica gel (0.05 – 0.2 mm; WOELM) as the stationary phase and acetic acid ethyl ester / petroleum ether (boiling point: 75° – 100° C) as the mobile phase.

Yield: 200 g (66.5 % of theory) boiling point: 118° C / 0.6 torr; molecular weight; calc. 599; (osmom.) found 586.

EXAMPLE 2

346 g of di-n-butylethanolamine were dissolved — as per example (1) — in 500 ml of acetonitrile and mixed with 140 ml of triethanolamine. At 30° C hexafluoropropene is introduced until the IR-spectroscope ceases to show any OH-bands. The reaction mixture is poured into 1 ltr of ice water, washed twice again with 1 ltr each of $H_2O$, dried over $Na_2SO_4$ and the last remnants of amine are eliminated at high vacuum.

yield: 459 g (71.1 % of theory) yield after distillation: 339 g (52.5 % of theory); boiling point: 52° C / 0.6 torr; molecular weight: calc. 323; (osmom.) found 318.

EXAMPLE 3

332 g of n-butyl-diethanolamine are dissolved as per example (1) in 1 ltr. of acetonitrile and mixed with 250 ml of triethylamine. Hexafluoropropene is introduced until the OH-bands have entirely disappeared. The reaction temperature is maintained at from 5° to 10° C. The work-up is carried out according to example (2).

yield: 820 g (88 % of theory); boiling point: 76° C / 0.3 torr; molecular weight: calc. 461; (osmom.) found 485.

EXAMPLE 4

300 g of N,N,N′,N′-tetrahydroxyethylhexamethylene-diamine [(HOCH$_2$—CH$_2$)$_2$N—(CH$_2$)$_6$—N(CH$_2$—CH$_2$OH)$_2$] are dissolved in 1 ltr. of acetonitrile and mixed with 300 ml of triethylamine. Hexafluoropropene is introduced at 5° – 10° C until the IR-spectroscope does not show free hydroxyl groups any longer. Work-up is carried out according to the aforecited examples.

Yield: 740 g (83 % of theory); molecular weight: calc.:892; (osmom.) found 706.

EXAMPLE 5

400 g of tris-(2-hydroxypropyl)-amine are dissolved — as per example (1) — in 600 ml of acetonitrile and mixed with 300 ml of triethylamine. Hexafluoropropene is introduced at a temperature of 30° – 35° C until the IR-spectroscope does not show OH-groups any longer. Work-up is performed as described above.

Yield: 426 g (63.5 % of theory); boiling point: 90° C / 1.5 torr;
molecular weight: calc. 641; (osmom.) found 602;

The addition of hexafluoropropene to alkanol amines proceeds at a higher speed than the oligomerization, so that the oligomerization of any entrained hexafluorpropene can be carried out after complete reaction of all the hydroxyl groups.

What is claimed is:

1. Fluorine-containing tert. amine having the formula

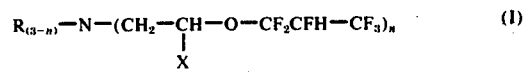

wherein *n* represents an integer from 1 to 3, X is H or CH$_3$ and R represents identical or different alkyl groups having from 1 to 12 carbon atoms or, if *n* is 2, represents the group

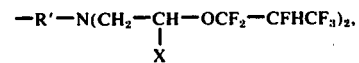

R′ being an alkylene group having from 2 to 12 carbon atoms.

2. Compound according to claim 1 having the formula

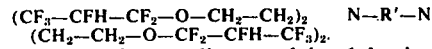

3. Compound according to claim 1 having the formula

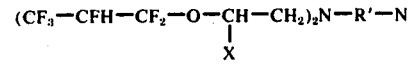

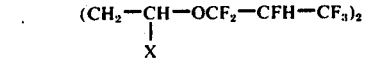

wherein R′ is an alkylene group having from 2 – 6 carbon atoms.

4. Compound according to claim 1 having the formula

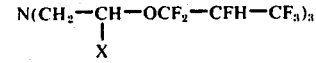

5. Compound according to claim 1 having the formula $$R_2N-CH_2-CH_2-OCF_2-CFH-CF_3$$

wherein R stands for alkyl groups having from 1 to 4 carbon atoms.

6. Compound according to claim 1 having the formula $$F R N (CH_2-CH_2-CH_2-OCF_2-CFH-CF_3)_2$$

wherein R stands for an alkyl group having from 1 – 4 carbon atoms.

7. Process for preparing a compound according to claim 1 which consists in reacting a compound having the formula $$R_{(3-n)}-N-(CH_2CH\ OH)_n \qquad (II)$$
$$\phantom{R_{(3-n)}-N-}|$$
$$\phantom{R_{(3-n)}-N-}X$$

wherein R, X and $n$ have the same meaning as in claim 1, with hexafluorpropene in the presence of a tertiary alkyl amine catalyst in an aprotic solvent at a temperature between −30° and +100° C.

* * * * *